(12) United States Patent
Hoheisel et al.

(10) Patent No.: US 8,658,213 B2
(45) Date of Patent: Feb. 25, 2014

(54) HYDROPHILIC NANOPARTICLES WITH FUNCTIONAL SURFACE GROUPS, PRODUCTION AND USE THEREOF

(75) Inventors: Werner Hoheisel, Köln (DE); Karlheinz Hildenbrand, Krefeld (DE)

(73) Assignee: Bayer Intellectual Property GmbH, Monheim (DE)

( * ) Notice: Subject to any disclaimer, the term of this patent is extended or adjusted under 35 U.S.C. 154(b) by 769 days.

(21) Appl. No.: 11/916,067

(22) PCT Filed: May 27, 2006

(86) PCT No.: PCT/EP2006/005087
§ 371 (c)(1),
(2), (4) Date: Feb. 7, 2008

(87) PCT Pub. No.: WO2006/131226
PCT Pub. Date: Dec. 14, 2006

(65) Prior Publication Data
US 2010/0086488 A1    Apr. 8, 2010

(30) Foreign Application Priority Data
Jun. 9, 2005   (DE) .......................... 10 2005 026 485

(51) Int. Cl.
*A61K 9/14*    (2006.01)

(52) U.S. Cl.
USPC ......................................................... 424/489

(58) Field of Classification Search
None
See application file for complete search history.

(56) References Cited

U.S. PATENT DOCUMENTS

| | | | |
|---|---|---|---|
| 4,613,483 A * | 9/1986 | Cohen | 422/131 |
| 6,322,901 B1 | 11/2001 | Bawendi et al. | |
| 6,423,551 B1 | 7/2002 | Weiss et al. | |
| 6,576,291 B2 | 6/2003 | Bawendi et al. | |
| 2005/0064604 A1 | 3/2005 | Bohmann et al. | |
| 2005/0239066 A1 * | 10/2005 | Asada et al. | 435/6 |

FOREIGN PATENT DOCUMENTS

| | | |
|---|---|---|
| EP | 1 473 347 A1 | 11/2004 |
| WO | 01 86299 A2 | 11/2001 |
| WO | 02 020695 A1 | 3/2002 |
| WO | 02 055186 A2 | 7/2002 |
| WO | WO 02055186 A2 * | 7/2002 |
| WO | 03 040024 A2 | 5/2003 |

OTHER PUBLICATIONS

Gao, In Vivo cancer targeting and imaging with semiconductor quantum dots, Nature Biology, 22, 8, 969-976.*

* cited by examiner

*Primary Examiner* — Paul Dickinson
(74) *Attorney, Agent, or Firm* — Norris McLaughlin & Marcus PA

(57) ABSTRACT

Nanoparticles having a hydrophilic surface coatings having biological, molecular biological, biochemical and medical applications, and method for their production.

9 Claims, No Drawings

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthesized

<400> SEQUENCE: 1
ggcagcaacg cgacgcgcac c                                              21

<210> SEQ ID NO 2
<211> LENGTH: 21
<212> TYPE: DNA
<213> ORGANISM: Artificial Sequence
<220> FEATURE:
<223> OTHER INFORMATION: Synthesized

<400> SEQUENCE: 2
ggtgcgcgtc gcgttgctgc c                                              21
```

HYDROPHILIC NANOPARTICLES WITH FUNCTIONAL SURFACE GROUPS, PRODUCTION AND USE THEREOF

This is a 371 of PCT/EP2006/005087 filed 27 May 2006 (international filing date).

The present invention relates to nanoparticles having a hydrophilic surface coating, to methods of production thereof and to the use thereof in biological, molecular biological, biochemical and medical applications.

BACKGROUND OF THE INVENTION

The use of nanoparticles in in vivo or in vitro diagnostics, in therapy, in embryology and generally in many molecular biological or biochemical applications and also in drug screening has gained more and more importance in recent years. To this end, most applications require nanoparticles which have a hydrophilic surface in order to disperse them in biological environs, i.e. in an aqueous environment. Said nanoparticles should ideally be in a monoparticulate or monodispersed, i.e. non-agglomerated, form, in order to firstly prevent unwanted sedimentation and/or secondly influence as little as possible the dynamics or kinetics of biochemical or biomolecular processes or motions. Furthermore, said nanoparticles should ideally have functional, reactive chemical groups enabling functional molecules to be coupled thereto. Functional molecules may be, for example, biological macromolecules such as, for example, oligonucleotides (e.g. DNA or RNA) or polypeptides (e.g. proteins or antibodies), biological coupling molecules such as, for example, biotin or streptavidin, or other organic molecules.

Fluorescent, inorganic nanoparticles are frequently prepared in organic solvents, resulting in hydrophobic final products. The most commonly used fluorescent, inorganic nanoparticles are semiconductor nanoparticles consisting of II-VI or semiconductors which usually have a core-shell structure. U.S. Pat. No. 6,322,901, U.S. Pat. No. 6,576,291 and U.S. Pat. No. 6,423,551 describe these particles whose inorganic core has a size of less than 10 nm and which are also referred to as "quantum dots". Due to their preparation, they frequently have an organic shell consisting of trioctylphosphine.

Another class of fluorescent, inorganic nanoparticles are phosphorescent nanoparticles which consist of nonconductive materials and which are doped with ions of the rare earth and/or transition group elements.

They are also referred to as nanophosphors, with WO 04/046035 A1, WO 02/020695 A1, K. Koempe; H. Borchert; J. Storz; A. Arun; S. Adam; T. Moeller; M. Haase; Angewandte Chemie, International Edition (2003), 42(44), 5513-5516 describing "down-converting nanophosphors" whose emission wavelength is longer than that of excitation, and in S. Heer; O. Lehmann; M. Haase; H. Guedel; Angewandte Chemie, International Edition (2003), 42(27), 3179-3182 describing "up-converting phosphors" whose emission wavelength is shorter than that of excitation.

WO 01/86299 A1, WO 03/040024 A1 describe the use of such nanophosphors also as biolabels.

WO 02/020695 A1 describes nanophosphors made of $CePO_4$:Tb and their preparation, for example in tris-ethyl hexyl phosphate (TEHP), producing particles comprising TEHP adhering to their surface. It is also possible to use tributyl phosphate or other hydrophobic derivatives of the phosphates rather than TEHP. While nanoparticles produced in this way cannot be dispersed in water, they can be dispersed in organic solvents, i.e. converted to monoparticulate suspensions.

However, a hydrophilic surface of the nanophosphors is an absolute requirement for the intended application in biological systems. The hydrophilization of nanoparticles having a hydrophobic surface is known in principle, as described in WO 02/055186 (Quantum Dot Corp.). There, hydrophilization of the hydrophobic nanoparticles is carried out with the aid of amphiphilic dispersers which are prepared, for example, by partially reacting polyacrylic acid with octylamine.

In the aqueous phase, the hydrophobic octylamide side chains interact with the hydrophobic surface of the nanoparticles, while the free acrylic acid groups of the amphiphilic disperser are oriented toward the aqueous phase. To the acrylic acid residues oriented in this manner, further molecules, for example, proteins or other biological macromolecules, can be attached via covalent bonds. The amphiphilic disperser here serves as a linker.

A disadvantage of this method is the relatively complex preparation of the hydrophobicized polyacrylic acid derivatives, which are utilized as amphiphilic dispersers, in a reproducible quality and also the relatively large space needed, due to the hydrophobic interaction of the hydrophobic surface of the nanoparticles with the octylamide groups of the amphiphilic polymeric disperser. Nanoparticles modified in this way have a greatly increased average particle size in comparison with the unmodified primary particles, even in the case of monoparticulate dispersion. This increase in volume is disadvantageous for various biological applications in which, for example, the labeled molecules are intended to penetrate biomembranes (e.g. cell wall) or diffuse through channel proteins. It is particularly disadvantageous for the use in homogeneous assays in which a (fluorescence) resonance energy transfer, (F)RET, to a (F)RET partner in spatial proximity is involved in the optical evaluation.

Based on the abovementioned prior art, it is therefore the object to provide inorganic nanoparticles having a hydrophilic surface, without a large increase in the average particle diameter, which nanoparticles preferably have reactive, functional chemical groups, thereby allowing functional molecules to be coupled thereto, and which can be used for biological, molecular biological, biochemical and medical, such as, for example, for diagnostic and therapeutic applications, in particular in homogeneous biological assays based on resonance energy transfer processes, and which, at the same time, are inexpensive and can be readily prepared.

SUMMARY OF THE INVENTION

This object is achieved by providing the nanoparticles of the invention. The nanoparticles of the invention are inorganic nanoparticles with an average particle size of from 1 nm to 500 nm, preferably from 1 nm to 100 nm, particularly preferably 1 nm to 40 nm, very particularly preferably 1 to less than 20 nm. The nanoparticles are luminescent, magnetic or scatter or absorb electromagnetic radiation, in particular in a manner enhanced by plasmon resonance excitation. The nanoparticles of the invention are equipped with a hydrophilic surface coating comprising at least one polymer and are characterized in that said surface coating has a low thickness of from 0.5 nm to 7 nm, preferably 0.5 to 4 nm, particularly preferably 0.5 to 2 nm.

A crucial difference of these polymeric dispersers in comparison with those described in WO 02/055186 A1 is the fact that they do not have any hydrophobic side chains enveloping the nanophosphors via hydrophobic interactions. As a result, the average particle diameter of the inventive nanoparticles modified with the polymers of the invention is distinctly smaller than those particles accessible via the "hydrophobic enveloping method" mentioned in WO 02/055186, which is advantageous to many applications. Such applications include, for example, those in which the nanoparticles act as partners for (fluorescence) resonance energy transfer, and/or those in which the nanoparticles are subjected to transport processes. Aside from their thin shell, the nanoparticles of the invention have the additional advantage of having high stability to influences from temperature, salt and pH.

DETAILED DESCRIPTION

Materials suitable in accordance with the invention for the nanoparticles are those comprising inorganic cores, whose crystal lattices (host material) are doped with foreign ions. These include in particular any materials and classes of materials which are used as "phosphors", for example in fluorescent screens (e.g. for electron ray tubes) or as coating material in fluorescent lamps (for gas-discharge lamps), as described, for example, in Ullmann's Encyclopedia of Industrial Chemistry, WILEY-VCH, 7th edition, 2004 Electronic Release, Chapter "Luminescent Materials: 1. Inorganic Phosphors". Aside from the down-converting phosphors which emit light of lower energy than they absorb, up-converting phosphors which emit light of higher energy than they absorb may also be used. In all of these materials, the foreign ions serve as activators for the emission of fluorescent light after excitation by UV light, visible or IR light, X-rays or gamma rays or electron rays. In some materials, also a plurality of types of foreign ions are incorporated into the host lattice, in order to first generate emission activators and secondly render excitation of the particle system more efficient or adjust the absorbance wavelength by shifting to the wavelength of a given excitation light source ("sensitizers"). The incorporation of a plurality of types of foreign ions may also serve to specifically set a particular combination of fluorescent bands to be emitted by a nanoparticle.

Materials suitable in accordance with the invention for the nanoparticles are also those having a layered structure (core-shell structure with one or more shells) of suitable materials. This involves foreign ions being incorporated in the host lattice in at least one part, core or at least one shell. The host material of the lad nanoparticles on which the nanoparticles of the invention are based preferably consists of compounds of the XY type. Here, X is a cation of elements of the main groups 1a, 2a, 3a, 4a, the transition groups 2b, 3b, 4b, 5b, 6b, 7b, or the lanthanides of the periodic table. In some cases, X may also be a combination or mixture of said elements. Y may be an anion comprising multiple atoms of one or more element(s) of the main groups 3a, 4a, 5a, the transition groups 3b, 4b, 5b, 6b, 7b and/or 8b and of elements of the main groups 6a and/or 7a. However, Y may also be a single atom anion of the main group 5a, 6a or 7a of the periodic table. The host material of the lad nanoparticles on which the nanoparticles of the invention are based may also consist of an element of the main group 4a of the periodic table. Elements of the main groups 1a, 2a or of the group comprising Al, Cr, Tl, Mn, Ag, Cu, As, Nb, Nd, Ni, Ti, In, Sb, Ga, Si, Pb, Bi, Zn, Co and/or elements of the lanthanides may be used for doping. Combinations of two or more of these elements in different relative concentrations to one another may also be used as doping material. The concentration of the doping material in the host lattice is between $10^{-5}$ mol % and 50 mol %, preferably between 0.01 mol % and 30 mol %, particularly preferably between 0.1 mol % and 20 mol %. The doping material is chosen for the fluorescence induced by it to have a long decay time (>100 ns).

Preference is given to using as host materials for the nanoparticles sulfides, selenides, sulfoselenides, oxysulfides, borates, aluminates, gallates, silicates, germanates, phosphates, halophosphates, oxides, arsenates, vanadates, niobates, tantalates, sulfates, tungstenates, molybdates, alkalihalides, fluorides and other halides or nitrides. Preference is given to using mixed lattices comprising a combination of the classes of materials mentioned. Examples of these classes of materials, together with the corresponding dopings, are indicated in the following list (materials of the B:A type, where B=host material and A=doping material, wherein A may also be mixtures of the materials indicated):

LiI:Eu; NaI:Tl; CsI:Tl; CsI:Na; LiF:Mg; LiF:Mg,Ti; LiF:Mg,Na; $KMgF_3$:Mn; $Al_2O_3$:Eu; $BaFCl$:Eu; $BaFCl$:Sm; BaFBr:Eu; $BaFCl_{0.5}Br_{0.5}$:Sm; $BaY_2F_8$:A (A=Pr, Tm, Er, Ce); $BaSi_2O_5$:Pb; $BaMg_2Al_{16}O_{27}$:Eu; $BaMgAl_{14}O_{23}$:Eu; $BaMgAl_{10}O_{17}$:Eu; $BaMgAl_2O_3$:Eu; $Ba_2P_2O_7$:Ti; $(Ba,Zn,Mg)_3Si_2O_7$:Pb; $Ce(Mg,Ba)Al_{11}O_{19}$; $Ce_{0.65}Tb_{0.35}MgAl_{11}O_{19}$:Ce,Tb; $MgAl_{11}O_{19}$:Ce,Tb; $MgF_2$:Mn; MgS:Eu; MgS:Ce; MgS:Sm; MgS:(Sm,Ce); (Mg,Ca)S:Eu; $MgSiO_3$:Mn; $3.5MgO.0.5MgF_2.GeO_2$:Mn; $MgWO_4$:Sm; $MgWO_4$:Pb; $6MgO.As_2O_5$:Mn; $(Zn,Mg)F_2$:Mn; $(Zn_4Be)SO_4$:Mn; $Zn_2SiO_4$:Mn; $Zn_2SiO_4$:Mn,As; ZnO:Zn; ZnO:Zn,Si,Ga; $Zn_3(PO_4)_2$:Mn; ZnS:A (A=Ag, Al, Cu); (Zn,Cd)S:A (A=Cu, Al, Ag, Ni); $CdBO_4$:Mn; $CaF_2$:Mn; $CaF_2$:Dy; CaS:A (A=lanthanides, Bi); (Ca,Sr)S:Bi; $CaWO_4$:Pb; $CaWO_4$:Sm; $CaSO_4$:A (A=Mn, lanthanides); $3Ca_3(PO_4)_2.Ca(F,Cl)_2$:Sb,$M_n$; $CaSiO_3$:Mn,Pb; $Ca_2Al_2Si_2O_7$:Ce; $(Ca,Mg)SiO_3$:Ce; $(Ca,Mg)SiO_3$:Ti; $2SrO.6(B_2O_3).SrF_2$:Eu; $3Sr_3(PO_4)_2.CaCl_2$:Eu; $A_3(PO_4)_2.ACl_2$:Eu (A=Sr, Ca, Ba); $(Sr,Mg)_2P_2O_7$:Eu; $(Sr,Mg)_3(PO_4)_2$:Sn; SrS:Ce; SrS:Sm,Ce; SrS:Sm; SrS:Eu; SrS:Eu,Sm; SrS:Cu,Ag; $Sr_2P_2O_7$:Sn; $Sr_2P_2O_7$:Eu; $Sr_4Al_{14}O_{25}$:Eu; $SrGa_2S_4$:A (A=lanthanides, Pb); $SrGa_2S_4$:Pb; $Sr_3Gd_2Si_6O_{18}$:Pb,Mn; $YF_3$:Yb,Er; $YF_3$:Ln (Ln=lanthanides); $YLiF_4$:Ln (Ln=lanthanides); $Y_3Al_5O_{12}$:Ln (Ln=lanthanides); $YAl_3(BO_4)_3$:Nd,Yb; $(Y,Ga)BO_3$:Eu; $(Y,Gd)BO_3$:Eu; $Y_2Al_3Ga_2O_{12}$:Tb; $Y_2SiO_5$:Ln (Ln=lanthanides); $Y_2O_3$:Ln (Ln=lanthanides); $Y_2O_2S$:Ln (Ln=lanthanides); $YVO_4$:A (A=lanthanides, In); $YVO_4$:A, Bi (A=lanthanides, In); $Y(P_xV_{1-x})O_4$:Eu (0<=x<=1); $Y(P_xV_{1-x})O_4$:Eu, Bi (0<=x<=1); $YTaO_4$:Nb; $YAlO_3$:A (A=Pr, Tm, Er, Ce); YOCl:Yb,Er; $Ln1PO_4$:Ln2 (Ln1, Ln2=lanthanides or mixtures of lanthanides); $A_x(PO_4)_y$:Ln (A=alkaline earth elements, Ln=lanthanides) $LuVO_4$:Eu; $GdVO_4$:Eu; $Gd_2O_2S$:Tb; $GdMgB_5O_{10}$:Ce,Tb; LaOBr:Tb; $La_2O_2S$:Tb; $LaF_3$:Nd,Ce; $BaYb_2F_8$:Eu; $NaYF_4$:A (A=Yb, Er, Tm, Ho); $NaGdF_4$:Yb, Er; $NaLaF_4$:Yb,Er; $LaF_3$:Yb,Er,Tm; $BaYF_5$:Yb,Er; $Ga_2O_3$:Dy; GaN:A (A=Pr, Eu, Er, Tm); $Bi_4Ge_3O_{12}$; $LiNbO_3$:Nd,Yb; $LiNbO_3$:Er; $LiCaAlF_6$:Ce; $LiSrAlF_6$:Ce; $LiLuF_4$:A (A=Pr, Tm, Er, Ce); $Li_2B_4O_7$:Mn, $SiO_x$:Er,Al (0≤x≤2).

Particular preference is given to using the following materials: $La_xCe_yTb_z$,$PO_4$ (x+y+z=1); $La_xEu_{1-x}PO_4$, $La_xSm_{1-x}PO_4$, $La_xDy_{1-x}PO_4$, $La_xNd_{1-x}PO_4$ (0<=x<1); $La_xCe_yLn_zPO_4$, (Ln=lanthanides, x+y+z=1); $MVO_4$:Ln (M=Y, Gd; Ln=lanthanides); $MVO_4$:Bi,Ln (M=Y, Gd; Ln=lanthanides); $MPO_4$:Ln (M=Y, Gd; Ln=lanthanides); $Y_xGd_{1-x}V_yP_{y-1}O_4$:Ln (0<=x<=1; 0<=y<=1; Ln=lanthanides); $Y_xGd_{1-x}V_yP_{y-1}O_4$:Bi,Ln (0<=x<=1; 0<=y<=1; Ln=lanthanides)$MSO_4$:Eu (M=Ca, Sr, Ba); $MSO_4$:Eu,Mn (M=Ca, Sr, Ba); $NaYF_4$:A (A=Yb, Er, Tm, Ho); ZnS:Tb, $ZnS:TbF_3$, ZnS:Eu, $ZnS:EuF_3$, $Y_2O_3$:Eu, $Y_2O_2S$:Eu, $Y_2SiO_5$:Eu, $SiO_2$:Dy, $SiO_2$:Al, $Y_2O_3$:Tb, CdS:Mn, ZnS:Tb, ZnS:Ag, ZnS:Cu. Among the particularly preferred materials, specifically those materials are selected which have a cubic lattice structure of the host lattice, since these materials result in a minimum number of individual fluorescent bands. Examples of these are: $MgF_2$:Mn; ZnS:Mn, ZnS:Ag, ZnS:Cu, CaSiO3:Ln, CaS:Ln, CaO:Ln, ZnS:Ln, $Y_2O_3$:Ln, or $MgF_2$:Ln (Ln=lanthanides).

Materials suitable in accordance with the invention for the nanoparticles are also those consisting of undoped, semiconducting materials. They include preferably those of the 4th main group (e.g. Si) and binary compounds AB, wherein A is an element of the 2nd transition group and B is an element of the 6th main group of the periodic table (e g ZnS, CdS or CdSe). They also include preferably those binary compounds AB, wherein A is an element of the 3rd main group and B is an element of the 5th main group of the periodic table (e.g. InAs, InP, GaAs, GaP or GaN).

The size of the inorganic nanocores suitable for the nanoparticles of the invention is within the range from 1 nm and 500 nm, preferably from 1 nm to 100 nm and particularly preferably from 1 nm to 40 nm, very particularly preferably from 1 to less than 20 nm.

The inorganic nanocores may have particular properties required for the particular application, for example properties of scattering or absorbing luminescent, electromagnetic radiation, it being possible to enhance said scattering or absorption by plasmon resonance excitation, magnetic properties (caused by atomic nuclei or electron shells), mechanical properties or other properties, depending on their purpose of usage. They may also be employed as partners in resonance energy transfer processes (FRET=fluorescence resonance energy transfer or Förster transfer), as described, for example, in "Principles of Fluorescence Spectroscopy"; J. R. Lakowicz, 2nd edition, Kluwer Academic, New York 1999, pages 367-442.

The hydrophilic polymers present in the envelope of the nanoparticles of the invention are preferably hydrophilic linear or branched homo- or copolymers, with functional groups such as amino, carboxyl or salts thereof, hydroxyl, thiol, acid anhydride, acid chloride and/or isocyanate groups which enable covalent or adsorptive, such as, for example, electrostatic, or ionic binding to the functional groups of the biomolecules to be coupled thereto.

In this context, the functional, possibly also adsorptive reacting groups of the corresponding polymers may be present in the repeat unit, such as, for example, in polyacids, polyacid anhydrides, polyalcohols, polythiols or polyamines or polyheterocycles, such as in the case of polyacrylic acid and/or its salts, polymethacrylic acid and/or its salts, poly (meth)acrylamides, polymaleic acid and/or its salts, polyaspartic acids and/or its salts, polymaleic anhydrides, polyethyleneimines, polyhydroxyethyl methacrylates (PHEMA), polydimethylaminoethyl methacrylates and/or its salts, polyvinylpyrrolidones, polyvinylalcohols, polyvinylacetals or polyvinyl ethers or polyethers.

Examples of aminic polymers suitable as homo- or copolymers are polyallylamine, polyvinylamine, linear or branched polyethyleneimines, polylysine, polymer-containing chitosamines and also polydiallyldimethylammonium chloride and/or polyvinylpyridine or their acid adducts.

All of the polymers mentioned may be used for preparing the nanoparticles of the invention as homopolymers or else as copolymers with one another and also with other monomers. Likewise conceivable are copolymers of acrylic acid with vinylpyrrolidone, maleic anhydride with methyl vinyl ether, vinylpyrrolidone with dimethylamino ethyl methacrylate, vinylimidazole with vinylpyrrolidone and methacrylic acid with vinylpyrrolidone.

Other suitable polymers are those whose functional groups are located in the terminal groups, such as, for example, in the case of polyethers whose terminal groups are functionalized by amino/carboxy/thio/isocyanate or otherwise, such as, for example in amino functional oligo- or polyethylene glycols (Jeffamine) or OH-terminated polyethylene oxides.

Preference is given to polymers with functional groups in the repeat unit, particularly preferably to polyacids, and here very particularly preferably to polyacrylic acids or polymethacrylic acids and/or their salts.

In another embodiment, it is also possible to use reactive polymers such as polymaleic anhydrides or polysuccinimides which, in the course of further processing, react to give the abovementioned polyelectrolytes, namely polyacrylic acid and polyaspartic acid, respectively.

In a preferred embodiment of the nanoparticles of the invention, their shell comprises polymethacrylic acids, polyaspartic acid (PASP), polymaleic acid, copolymers of acrylic acid, for example with maleic acid, which are supplied by BASF under the product name Sokalane®, and/or copolymers of acrylic acid with maleic acid and vinyl ether, which are supplied by SKW Polymers under the name Melpers®, and/or their salts, preferably their sodium salts.

Particular preference is given to the presence of sodium polyacrylates in the shell of the nanoparticles of the invention.

The molecular weight ($M_W$) of the "enveloping polymer" may vary, and is preferably from 1000 to 100 000 gmol$^{-1}$, preferably from 1000 to 25 000 gmol$^{-1}$, particularly preferably from 5000 to 12 000 gmol$^{-1}$, and very particularly preferably from 7000 to 10 000 gmol$^{-1}$.

Thus, sodium polyacrylates with a molecular weight $M_W$ of approx. 8000 gmol$^{-1}$ were found to produce better results than the corresponding higher molecular weight analogs with a molecular weight of 50 000 gmol$^{-1}$, for example.

The hydrophilic surface shell of the nanoparticles of the invention may also have particular properties required for the particular application which complement those of the inorganic nanocores, such as, for example, fluorescent properties, properties of scattering or absorbing electromagnetic radiation, magnetic properties (caused by atomic nuclei or electron shells) or other properties, depending on their purpose of usage. They may also be used as partners in resonance energy transfer processes (Forster transfer).

Particular preference is given to nanoparticles of the invention comprising $CePO_4$:Tb as inorganic nanocore and having a hydrophilic surface envelope comprising the sodium salt of polyacrylic acid. Said nanoparticles are distinguished by high stability to relatively high electrolyte concentrations. Thus, for example, even in 2 molar NaCl solutions sufficient suspension stability was observed. Preferably, however, concentrations of one mol for monovalent ions and 0.5 mol for polyvalent ions such as $MgCl_2$ should not be exceeded.

Moreover, the nanoparticle suspensions of the invention have high temperature stability. Thus it was possible to treat a $CePO_4$:Tb nanoparticle suspension enveloped by polyacrylic acid, sodium salt, with boiling water over half a day, without losing suspension stability. Preferably, the nanoparticle suspensions of the invention may be treated with hot water at 95° C. once or several times for 3 to five hours, with no substantial losses. This meets the basic conditions, for example for qPCR detection methods.

Laser light scattering or, preferably, the use of analytical ultracentrifugation (AUC) is suitable for determining the particle size and for detecting the monodispersity of the nanoparticles of the invention. AUC is known to the skilled worker, as described, for example, by H. G. Müller in Colloid & Polymer Science 267:1113-1116.

A proven method of determining the surface charge is especially gel electrophoresis whose basic principles are described, for example, by R. Westermeier "Electrophoresis in Practice" Wiley-VCH.

Another method for surface characterization is zeta-potential determination, as described, for example, by Hiemenz and Rajagopalan, Principles of Colloid and Surface Chemistry, 3rd Edition, New York: Dekker 1997.

The thickness of the polymer shell layer may be determined by combined application of transmission electron microscopy, electron spectroscopy for chemical analysis (ESCA) and thermogravimetry (TGA) and is from 0.5 nm to 7 nm, preferably 0.5 to 4 nm, particularly preferably 0.5 to 2 nm.

The thickness of the polymer shell layer may, when using transmission electron microscopy, be observed directly, which, however, can only give a first indication due to the problems known to the skilled worker of preparation artifacts typical for transmission electron microscopy. ESCA can be used for establishing whether signals of the inorganic core of the enveloped nanoparticle can still be detected, indicating layer thicknesses of less than approx. 5 nm. With TGA, the polymer shell can be thermally desorbed from the nanoparticles and its absolute mass and also its mass relative to the nanoparticle can be determined. If the size of the inorganic portion of the nanoparticle, which can be determined by transmission electron microscopy, its density and the density of the polymer are known, the average polymer shell can thus be calculated. For example, if $CePO_4$:Tb nanoparticles with an inorganic particle size of 7 nm and a density of 5.2 $g/cm^3$, which are enveloped by a layer of polyacrylic acid with a density of 1.1 $g/cm^3$ in such a way that a relative weight loss of 20% occurs during TGA, a shell thickness of 1.0 nm is observed.

The invention likewise relates to a method of preparing the nanoparticles of the invention. Due to their preparation, for example owing to their synthesis in hydrophobic solvents, many types of nanoparticles have a hydrophobic surface. The method of the invention of preparing monodisperse, aqueous dispersions starting from hydrophobic nanoparticle agglomerates, involves at least partial dealkylation of the hydrophobic starting products by heating up in high-boiling, water-miscible solvents and subsequent enveloping with hydrophilic polymers by reacting the nanoparticles heated up as described with suitable polymers which preferably have functional, reactive groups, in water-miscible solvents, optionally with the use of solubilizers.

In order to enable affinity of the above-described hydrophilic polymeric dispersers to the hydrophobic nanoparticles to be hydrophilized, the latter must be dehydrophobicized completely or at least partially.

Surprisingly, it was found that dehydrophobicization or partial dehydrophobicization of, for example, nanophosphors modified with tris-ethyl hexyl phosphate (TEHP) or tributyl phosphate can be achieved by simple heating up in at least one high-boiling, preferably water-miscible solvent such as, for example, N-methylpyrrolidone (NMP), dimethylformamide (DMF), dimethylacetamide (DMAc), dimethyl sulfoxide (DMSO), triethyl phosphate or diethyl phosphite, or in mixtures of these solvents, preferably in pure NMP.

Dehydrophobicization is carried out by heating close to the boiling point, preferably to 180 to 250° C., particularly preferably to 200° C., for several hours, preferably 2 to 3 hours.

The polymer enveloping following dehydrophobicization may be carried out in principle in any, preferably the same solvent (dehydrophobicization solvent).

Said solvents may preferably be treated with "solubilizers", such as ethylene glycol, glycerol or low molecular weight oligoethylene glycols or their monomethyl ethers, preferably low molecular weight ethylene glycols, very particularly preferably ethylene glycol, in from a few percent by weight up to equal amounts. A particularly preferred solvent system comprises equal proportions by weight of NMP and ethylene glycol, as described in Example 2.

While dehydrophobicization, as described, can be carried out at high temperatures, polymer enveloping may be carried out by stirring or rolling at RT for several hours.

As described in Example 2, the dehydrophobicization solution is admixed with approximately equal amounts of ethylene glycol and an approx. 1% strength aqueous solution of the polymer to be enveloped, and is stirred preferably overnight, or continuously agitated on a roller bench.

The method of the invention likewise relates to working up of the reaction products. The enveloped nanoparticles may be separated from their byproducts by ultracentrifugation or a membrane process, preferably ultrafiltration (UF). For example, membranes of polyether sulfone, with a cut-off of 100 000 Da, are suitable for isolating the $CePO_4$:Tb nanoparticles prepared herein. In this case, the nanoparticles are retained, while the excess byproducts such as polymers or organic solvents permeate. The suitable size of the membrane cut-off can vary and depends on the size of the nanoparticles to be coated and the molecular weight of the polymer used. However, said size can be readily narrowed down by the skilled worker in the art.

The invention likewise relates to derivatives of the nanoparticles of the invention, which are accessible by chemical reactions, for example coupling of functional molecules to the hydrophilic surface coating, and/or by physical processes on and/or in the surface coating.

Thus it is possible to attach to the hydrophilic surface envelope of the nanoparticles of the invention, for example to CePO4:Tb, for example dyes such as fluorescein or rhodamine (e.g. Sigma-Aldrich, Taufkirchen, Germany), Bodipy, Alexa 546 (Molecular Probes, Eugene, USA), Cy3 (Amersham Bioscience, General Electric HealthCare), Atto 532, Atto 550 (Atto-Tec GmbH, Siegen, Germany) or other fluorescent dyes known to the skilled worker. In order to utilize a fluorescence resonance energy transfer (FRET), use is made here ideally of those dyes which, when used as acceptor, have a very high overlap between the absorption profile of the dye and the emission bands of the nanoparticle used as emitter. Suitable acceptor molecules, however, are also those which quench the fluorescence of the donor, without fluorescing themselves, such as, for example, Black Hole Quencher BHQ-1 (BIOSEARCH Technologies, Novato, USA). In this case too, those quencher molecules are used which have a very large overlap between the absorption profile of the quencher molecule and the emission bands of the nanoparticle used as emitter. With regard to said overlap, the wavelength of at least one emission peak of the fluorescent bands of the nanoparticle should preferably be within the range of the main absorption of the dye, with the wavelength units of the main absorption being defined by the 37% value of the absorption peak. In those cases, in which the emission wavelengths of the dyes overlap with absorption bands of the nanoparticle, the nanoparticles act as acceptors and the dyes as donors. In order to achieve an FRET as effective as possible, the information with regard to the location of absorption and emission bands is the same as above.

It is thus possible, with the aid of the thus modified nanoparticles of the invention, to further establish the distance between the inorganic nanocore and the dye and therefore indirectly the thickness of the polymer-containing hydrophilic surface envelope with the aid of a resonance energy transfer (Förster transfer) from the inorganic nanocores to the dye (Example 3).

The energy transfer may be measured firstly by the fluorescence of the dye sensitized by the nanoparticle. For this purpose, the nanoparticle is excited with a flashlight which produces a flash of a few microseconds or shorter, while the emission spectrum is measured after a delay, after which time the excitation light pulse has faded away. The length of the delay depends essentially on the illumination time of the excitation flashlight and is usually 20-50 microseconds. Due to this measuring principle, light emission of the directly excited dye or a possibly occurring background fluorescence is virtually completely eliminated. In such spectra, the donor's fluorescence reduced due to the energy transfer can be seen as being overlaid by the sensitized fluorescence of the acceptor. With a different measuring principle, the energy transfer may be determined by comparing the fluorescence lifetime of the inorganic nanocores with and without dye coupled thereto. The skilled worker can readily determine the efficiency of the energy transfer from the ratio of the lifetime and taking into account the finite size of the nanoparticles (and thus taking into account the spatial distribution of the emitter ions), and thereby infer the thickness of the polymer layer around the nanoparticles. The reduction in fluorescence lifetime, determined as a function of the number of coupled dye molecules, by up to 90% shows the high energy transfer efficiency of the systems described in the example. This is possible only if the distance between the inorganic nanocore and the dye is distinctly shorter than the critical distance for an energy transfer ("Förster radius") which is approx. 5 nm. This result is another clear indication of the low thickness of the polymer-containing surface envelope layer of the nanoparticles of the invention.

The invention likewise relates to the nanoparticles obtainable by additionally coupling thereto at least one functional molecule such as, for example, a general organic molecule or biological macromolecules such as, for example, antibodies or other proteins, peptides, enzymes, oligonucleotides or other nucleic acid molecules or nucleic acid-like molecules, such as PNAs or morpholinos, oligo- or polysaccharides, haptenes, such as biotin or digoxin, or low molecular weight synthetic or natural antigens or epitopes or coupling molecules such as avidin, streptavidin or neutravidin.

Preference is given to coupling oligonucleotides (Example 4), biotin, avidin and/or streptavidin (Examples 5 and 6) to the nanoparticles of the invention.

Physical processes in hydrophilic surface coating may be couplings of suitable ions via complex formation, such as, for example, paramagnetic ions (e.g. iron), which make further analytical methods possible. However, physical crosslinking by way of intramolecular complex formation and thus stabilization of the hydrophilic polymer-containing surface envelope is also possible.

In another embodiment of the invention, the functional groups of the envelope polymers may be crosslinked with bi- or higher functional low molecular weight molecules, such as, for example, with di-, tri-, tetra-, penta- or polyfunctional reagents such as lysine, ethylenediamine diacetate (EDDA). For example, the polyacrylate envelope polymer located on the inorganic nanocores was crosslinked by reacting with lysine, a bifunctional reagent (Example 7). It is also possible here for interparticulate crosslinking to occur to a small extent, which is observed on the basis of larger average particular diameters in comparison with those of the starting substances.

Particular preference is given to the lysine-crosslinked, fluorescein-modified $CePO_4$:Tb nanoparticles having sodium polyacrylate in the hydrophilic surface envelope. These nanoparticles display particularly strong donor and acceptor properties for fluorescence resonance energy transfer (FRET).

Chemical reactions which are used for derivatizing the surface envelope of the nanoparticles of the invention and/or physical processes in said surface envelope are known to the skilled worker and are described in standard books of organic chemistry or biochemistry.

The invention likewise relates to the use of the nanoparticles of the invention and/or their derivatives as biolabels in heterogeneous and homogeneous biological assays, for example in order to indicate quantitatively and/or qualitatively the presence of biological macromolecules to be detected, such as, for example, antibodies or other proteins, peptides, oligonucleotides or other nucleic acid molecules or nucleic acid-like molecules such as PNAs or morpholinos, oligo- or polysaccharides, haptenes. Such assays may be, for example, immunoassays in the formats known to the skilled worker in this field or else quantitative PCR assays, likewise in the formats known to the skilled worker (e.g. Molecular Beacon, Taqman, Dual Hybridization or Scorpions Format). Assay formats in which the target molecule is recognized due to induced agglomeration of the nanoparticles and a turbidity or change in the intensity or wavelength of absorption, light scatter or fluorescent light, can also be implemented using the nanoparticles of the invention. The nanoparticles may be excited here via a one photon or else multiple photon process.

It is also possible to use the nanoparticles of the invention as markers or labels in molecular and/or cell biology and in medical diagnostics or therapeutics. Here, the presence or absence of an analyte can be measured, cell sections can be stained or biological molecules or biologically active molecules labeled with the nanoparticles of the invention can be monitored in vivo or in vitro.

In addition, the nanoparticles of the invention may also be used as fillers or additives in polymers, in particular as additives in organic or inorganic paint or coating systems or as additives in inks.

The invention is illustrated in more detail below on the basis of the examples, without being limited thereto.

EXAMPLES

Preparation of a Hydrophobic Nanoparticulate Suspension 1.9 g of hydrophobic $CePO_4$:Tb nanoparticles were suspended in 19.0 g of NMP (N-methyl-pyrrolidone). This suspension was heated in a glass flask with magnetic stirrer and reflux condenser with stirring to 200° C. for 2 h. A brown, transparent nanoparticulate suspension was produced (20.9 g of a 9.1% strength suspension). An average particle size distribution of 5.4 nm ($d_{50}$ value) was determined for this NMP/nanoparticle suspension by means of analytical ultracentrifugation (AUC). A 1% strength suspension for the following polymer enveloping was produced by adding NMP.

Enveloping the Hydrophobic Suspension with Polyacrylic Acid Sodium Salt (PASNa)

10.0 ml of the 1% strength, hydrophobic NMP nanoparticle suspension were admixed with 10.0 ml of ethylene glycol (EG) in a 50 ml Falcon tube (made of PP, with screw cap). To this, 20.0 g of a PASNa/EG mixture (10.0 g of 1% strength PASNa solution MW: 8000 D, Aldrich and 10.0 g of EG) were added. This nanoparticulate suspension was mixed by rolling the Falcon tube overnight. The reaction mixture was worked up by means of ultrafiltration (UF) at approx. 3 bar in a 50 ml Millipore stirring cell with a polyether sulfone (PES) membrane whose cut-off was 100 000 Da. The solvent was exchanged by continuous permeation with water, with a total permeate volume of approx. 850 ml. The corresponding concentrate (retentate) comprised 15 ml of a 0.75% strength clear, colorless nanoparticulate suspension having the following properties:

pH: 7.0;

Particle size distribution (determined by AUC): $d_{50}$:5.9 nm;

Gel electrophoresis (GEP): in gel electrophoresis (agarose gel in Tris acetate EDTA buffer), the PASNa-enveloped nanoparticles migrate to the anode, while the nonenveloped, water-insoluble starting products did not have electrophoretic mobility.

Spectroscopic study: excitation at 280 nm produced the typical fluorescence peaks for light emission of terbium ions at 487 nm, 542 nm (main peak), 583 nm and 620 nm. The half lives of these emission peaks were 1.35 ms.

Stability to salt loads: the PASNa-enveloped nanophosphors proved to be very stable to salt concentrations. No agglomerations were produced up to a concentration of 2000 mmol+/l NaCl and up to 5 mmol/l $MgCl_2$.

Stability to pH variations: the PASNa-enveloped nanophosphors proved to be very stable to pH changes in the range from pH 4 to at least pH 9.

Temperature stability: the PASNa-enveloped nanophosphors proved to be very stable to high temperatures. The dispersions were able to be maintained at over 90° C. for more than 6 hours without a substantial change in particle size distribution or optical properties.

Coupling of Fluorescein to the PASNa-Enveloped Nanophosphors

The reaction was carried out in a 15 ml Falcon tube (PP). 1.5 ml of the abovementioned polyacrylic acid-Na-enveloped nanophosphors were admixed with 70 mg of EDC (1-ethyl-3-(3-dimethylaminopropyl) carbodiimide hydrochloride, Aldrich), dissolved in 1.5 ml of phosphate buffer (0.1 m, pH: 6.0), by pipetting. After vortexing, the reaction mixture was rolled on the roller bench at room temperature for 30 mins, resulting in a pH of 6.5. To this reaction mixture, 5 mg of fluoresceinamine (Fluka), dissolved in 7.5 ml of borate buffer (0.1 m, pH: 8.3) were added. After vortexing, the reaction mixture was rolled in the dark overnight, resulting in a pH of 8.3 in the yellow reaction medium.

Work up was carried out by way of ultrafiltration (PES membrane 100 000 D, approx. 3 bar) with water as permeant. After a permeation volume of 350 ml, an absolutely colorless permeate was obtained after an initially yellow permeate. The concentrate (product) was a brightly yellow, transparent nanoparticulate suspension having the following properties:

Volume: 2.2 ml
Nanoparticle concentration: 0.5% by weight
Particle size distribution (AUC): $d_{50}$:8.4 nm
Spectroscopic study (Jobin Yvon, Fluorolog FL3-22 with phosphorescence option): for this purpose, the particle distributions were diluted to a concentration of 0.002% by weight and excited at 280 nm with a Xe flashlight. The energy transfer was measured firstly by way of the fluoresceins sensitized by the $CePO_4$:Tb nanophosphors. For this purpose, the fluorescence spectrum was recorded after a delay of 40 µs after the excitation light pulse, in order to virtually completely eliminate light emission of the directly excited dye or a possibly occurring background fluorescence. The fluorescence peaks typical for light emission of terbium ions at 487 nm, 542 nm (main peak), 583 nm and 620 nm appeared, with a broad background peak centered at 523 nm, which indicates the sensitized fluorescein fluorescence. Secondly, the energy transfer was determined by comparing the fluorescence lifetime of the $CePO_4$:Tb nanophosphors at a wavelength of 542 nm with and without coupled fluorescein. This resulted in a reduction of the lifetime by up to 90%. Even taking into account that several fluorescein molecules were coupled, this result demonstrates the high FRET efficiency of the system present herein, which is possible only if the distance between the nanophosphor and dye is distinctly smaller than the critical distance of an FRET ("Förster radius") which is approx. 5 nm.

In control experiments in which the fluroescein molecules were added without coupling to the nanophosphors, no time-delayed emission of fluroescein at 523 nm was observed. Likewise, the half life did not change compared with the measurements in which the polyacrylic acid-Na-enveloped nanophosphors were present alone.

Coupling of Oligonucleotides to the PASNa-Enveloped Nanophosphors

To 0.8 ml of the nanophosphor/PASNa particle suspension described in Example 2, 65 mg of EDC dissolved in 0.5 m phosphate buffer, pH 6.0 were added. This was followed by mixing at room temperature (RT) for 1 h, which produced a pH of 6.2.

The thus activated nanophosphors were admixed with 1.9 mg of the following NH-oligosequence (Thermo Electron, Ulm), dissolved in 0.4 ml of borate buffer 0.2 m, pH: 9: 5' GGC AGC AAC GCG ACG CGC ACC-3'(5' aminolink C6/MMT).

After incubating with stirring at RT for 4 hours, the mixture was stored at 4° C. overnight and subsequently purified by means of ultrafiltration using a Vivaspin cell (VivaScience, PES membrane MWCO 50 000 D).

The final product (0.8 ml) was a 1.2% strength clear nanoparticulate suspension

This final product was diluted by a factor of 5 and incubated with the 6-fold molar concentration of the complementary sequence 5' GGT GCG CGT CGC GTT GCT GCC 3' (3' TAMRA; TAMRA=rhodamine derivative, Thermo Electron, Ulm), together with 1.5 mM $MgCl_2$. The fluorescence lifetime of the light emission of the nanophosphors at a wavelength of 542 nm was subsequently measured similarly to Example 3. The result was a shortening of the lifetime by 70% which was caused by the FRET from the nanophosphor to the TAMRA dye.

Coupling of Biotin to the PASNa-Enveloped Nanophosphors (HIE 13 024)

24 mg of EDC were dissolved in 0.04 ml of 0.5 m phosphate buffer pH 6.0 and added to 0.09 ml of PASNa-enveloped nanophosphors (product of Example 2). After incubating at RT for 1 h, 3.745 mg of biotin-(PEO)3-amine (Bioscience 00215), dissolved in 0.05 ml of 0.2 m borate buffer pH 9.2, were added. After a reaction time with stirring of 6 hours, the mixture was stored at 4° C. overnight and subsequently purified by means of ultrafiltration (Vivaspin MWCO 50 000 PES membrane).

Biotin coupling was detected by diluting the dispersion in PBS buffer at pH 8 to 800 µg/l and adding it to a dispersion (800 µg/l) containing strepatavidin-enveloped magnetic polymer beads (Sera-Mag® Strepatavidin, Serva, Heidelberg). The polymer beads were subsequently removed for 10 minutes using a permanent bar magnet and the fluorescence of the supernatant was measured. No fluorescence was visible, while a distinct fluorescence of the nanophosphors was detected prior to adding the polymer beads. This experiment demonstrates good coupling of the biotin to the nanophosphors.

Coupling of Streptavidin to the PASNa-Enveloped Nanophosphors

To 0.3 ml of a 6% strength PASNa-modified nanophosphor suspension (product of Example 2), 40 mg of EDC and 30 mg of SulfoNHS (N-hydroxysuccinimide), dissolved in 0.5 m phosphate buffer, pH 6.0, were added. Incubation with mixing was carried out at RT for one hour. Subsequently the activated nanophosphors were isolated by means of ultrafiltration (PES membrane MWCO: 100 000 D). The retentate obtained was a slight opaque suspension with pH 5.7.

To 1 ml of this particle suspension, 5.0 mg of streptavidin (Sigma S4762), dissolved in 0.2 m borate buffer, pH 9.2, were added. After incubating for 4 hours and storage at 4° C. overnight, the final product was purified by ultrafiltration (PES membrane MWCO 100 000 D), resulting in a 1.3% strength clear solution with pH 8.3 as retentate. Streptavidin binding was detected similarly to detecting biotin binding in Example 5, except that the positions of streptavidin and biotin were exchanged.

Crosslinking of the PASNa-Enveloped Nanophosphors with Lysine

To 5 ml of the PASNa-enveloped nanophosphors (1.1% strength suspension) described in Example 2, 170 mg of EDC dissolved in 5 ml of 0.1 m phosphate buffer pH 6.0 were added. The mixture was incubated at RT for 30 minutes, with mixing on a roller bench.

This was followed by adding 4.34 mg of L-lysine dissolved in 2.5 ml of 0.2 m borate buffer pH 9.0.

After 24 h of incubation at RT, the mixture was stored at 4° C. overnight and then purified by means of ultrafiltration (PES membrane 100 000 MWCO).

Intraparticulate crosslinking was detected via IR spectroscopy on the basis of the amide groups.

The invention claimed is:

1. Inorganic nanoparticles with an average particle size of from 1 nm to 500 nm, enveloped with a coating of a hydrophilic polymer having no hydrophobic side chains, said nanoparticles having luminescent, magnetic or electromagnetic radiation scattering or absorbing properties, said properties being of a kind that are enhanced by plasmon resonance excitation, wherein said coating has a thickness of from 0.5 nm to 7 nm and said hydrophilic polymer is polyacrylic acid sodium salt, having an average molar mass from 5,000 to 12,000 g/mol.

2. The inorganic nanoparticles of claim 1, having a crystal lattice doped with foreign ions.

3. The inorganic nanoparticles of claim 1 having donor or acceptor properties for fluorescence resonance energy transfer.

4. The inorganic nanoparticles of claim 1 wherein at least one functional molecule or a biomolecule is chemically or physically attached to the hydrophilic coating.

5. The inorganic nanoparticles of claim 1 wherein the hydrophilic polymer is crosslinked.

6. A method of preparing the inorganic nanoparticles of claim 1, which comprises heating hydrophobic nanoparticles to a temperature of 180° C. to 250° C. in a solvent selected from the group consisting of N-methylpyrrolidone (NMP), dimethylformamide, (DMF), dimethylacetamide (DMAc), dimethyl sulfoxide (DMSO), triethyl-phosphate or diethyl-phosphite, or mixtures thereof, and reacting said nanoparticles with a solution of a hydrophilic polymer in the same or at least one other water-miscible solvent and wherein said hydrophilic polymer is polyacrylic acid sodium salt, having an average molar mass of from 5,000 to 12,000 g/mol.

7. Biolabels in heterogeneous or homogeneous biological assays comprising the inorganic nanoparticles of claim 1.

8. Markers or labels in molecular and/or cell biology, in medical diagnostics or therapeutics comprising the inorganic nanoparticles of claim 1.

9. Polymers, organic or inorganic paints or coating systems, or inks comprising the inorganic nanoparticles of claim 1.

* * * * *